United States Patent
Kloeffel et al.

(10) Patent No.: US 11,007,115 B2
(45) Date of Patent: May 18, 2021

(54) CONTAINER, USE, DIALYZER OR PREPARATION UNIT AS WELL AS METHOD OF MANUFACTURING A CONCENTRATE

(71) Applicant: FRESENIUS MEDICAL CARE DEUTSCHLAND GMBH, Bad Homburg (DE)

(72) Inventors: Peter Kloeffel, Nuedlingen (DE); Gerhard Wiesen, Bad Homburg (DE); Francois D'Ayot, Lyons (FR); Philippe Laffey, Sainte Foy les Lyon (FR); Benoit Luaire, Sourcieux les Mines (FR)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/017,040

(22) Filed: Jun. 25, 2018

(65) Prior Publication Data

US 2018/0303711 A1 Oct. 25, 2018

Related U.S. Application Data

(63) Continuation of application No. 13/537,280, filed on Jun. 29, 2012, now Pat. No. 10,022,297.

(60) Provisional application No. 61/503,808, filed on Jul. 1, 2011.

(51) Int. Cl.
*A61J 1/10* (2006.01)
*A61M 1/16* (2006.01)

(52) U.S. Cl.
CPC .............. *A61J 1/10* (2013.01); *A61M 1/167* (2014.02); *A61M 1/1656* (2013.01); *A61M 1/1666* (2014.02); *A61M 1/1668* (2014.02)

(58) Field of Classification Search
CPC ............ A61M 1/1656; A61M 1/1666; A61M 1/1668; A61M 1/167; A61J 1/05; A61J 1/10
See application file for complete search history.

(56) References Cited

U.S. PATENT DOCUMENTS

| | | | |
|---|---|---|---|
| 4,664,891 A | 5/1987 | Cosentino | |
| 5,385,564 A * | 1/1995 | Slater | A61M 1/1656 128/898 |
| 5,616,305 A | 4/1997 | Mathieu | |
| 5,938,337 A * | 8/1999 | Provan | B65B 1/02 383/120 |
| 6,007,529 A * | 12/1999 | Gustafsson | A61J 1/00 604/410 |
| 6,361,209 B1 * | 3/2002 | LaRue | B65D 33/08 383/10 |

(Continued)

FOREIGN PATENT DOCUMENTS

| | | |
|---|---|---|
| CN | 1338952 | 3/2002 |
| CN | 101427978 | 5/2009 |

(Continued)

*Primary Examiner* — Patrick Orme
(74) *Attorney, Agent, or Firm* — Jacobson Holman PLLC

(57) ABSTRACT

A container includes a dry concentrate designed such that the dry concentrate forms an acid liquid concentrate, or a part of an acid liquid concentrate, which is suitable for manufacturing a dialysis solution, on the dissolution of the dry concentrate in a liquid, preferably in water.

8 Claims, 5 Drawing Sheets

(56) References Cited

U.S. PATENT DOCUMENTS

| | | | | |
|---|---|---|---|---|
| 6,572,268 | B2* | 6/2003 | Ichikawa | A61J 1/00 222/92 |
| 6,872,197 | B1* | 3/2005 | Witowski | B32B 15/08 206/438 |
| 7,635,222 | B2* | 12/2009 | Plourde | B65B 9/20 383/200 |
| 8,540,427 | B2* | 9/2013 | Steele | B65D 33/2575 383/120 |
| 2002/0091371 | A1 | 7/2002 | Ritter | |
| 2003/0168120 | A1* | 9/2003 | Brehm | A61M 1/1656 141/313 |
| 2005/0096625 | A1 | 5/2005 | Brandl | |
| 2006/0257056 | A1* | 11/2006 | Miyake | B65D 75/5805 383/103 |
| 2007/0138183 | A1 | 6/2007 | Ritter | |
| 2009/0320684 | A1* | 12/2009 | Weaver | A61M 1/1656 96/12 |
| 2010/0016825 | A1* | 1/2010 | Graf | A61M 1/1656 604/408 |
| 2011/0120946 | A1 | 5/2011 | Levin | |
| 2011/0137280 | A1* | 6/2011 | Ramella | A61M 1/1656 604/416 |
| 2012/0288572 | A1 | 11/2012 | Kugelmann | |
| 2013/0333795 | A1 | 12/2013 | Balschat | |
| 2014/0230923 | A1 | 8/2014 | Brehm et al. | |

FOREIGN PATENT DOCUMENTS

| | | | |
|---|---|---|---|
| CN | 101443056 | 5/2009 | |
| CN | 101495163 | 7/2009 | |
| CN | 101622021 | 1/2010 | |
| DE | 44 22 100 | 12/1995 | |
| DE | 101 00 549 | 7/2002 | |
| DE | 103 13 965 | 10/2004 | |
| DE | 602 07 683 | 7/2006 | |
| DE | 10 2005 060 290 | 12/2006 | |
| EP | 1 344 550 | 9/2003 | |
| FR | 2 766 797 | 2/1999 | |
| WO | WO 2011/073274 | 6/2011 | |
| WO | WO 2011/073274 A1 * | 6/2011 | A61M 1/16 |

* cited by examiner

CONTAINER, USE, DIALYZER OR PREPARATION UNIT AS WELL AS METHOD OF MANUFACTURING A CONCENTRATE

BACKGROUND OF THE INVENTION

1. Field of the Invention

The present invention relates to a container comprising at least one dry concentrate.

2. Description of Related Art

A base concentrate which is usually present as a dry concentrate consisting of or comprising bicarbonate is usually used as part of carrying out a dialysis treatment, in particular a hemodialysis treatment. This concentrate is located, for example, in a container such as a bag or a cartridge which is connected to the dialyzer. A saturated solution consisting of or comprising bicarbonate is then manufactured from this dry concentrate by supplying ultra-pure water. This base concentrate can be led off out of the container and be used for manufacturing the actual dialysis solution, with it being possible to start the leading off of the concentrate when solid dry concentrate is still located in the container.

A so-called acid concentrate is usually used in the manufacture of a dialysis solution in addition to the named base concentrate. It comprises a solution of a plurality of components which are usually present in different amounts and/or concentrations. Typical components are NaCl as the main component and the other electrolytes such as $CaCl_2$ and $MgCl_2$ in smaller amounts. The specifications for the concentrations of the electrolytes are very tight, which has the consequence that all the components of the acid concentrate have to be completely dissolved before the use of the acid concentrate in the proportioning or metering unit for manufacturing the dialysis solution. This cannot take place in flow as with the base concentrate. It is rather the case that special mixing apparatus such as stirrers have to be used here to ensure this complete dissolving in an acceptable time period.

Against this background, the named acid concentrate is usually supplied as a liquid concentrate in a canister from which the liquid concentrate is removed by means of the dialyzer or a preparation unit and is used for manufacturing the finished dialysis solution. A disadvantage in the use of such canisters is the comparatively complex handling as well as the relatively high weight, which brings about disadvantages with respect to the transportation costs and storage costs.

In clinics in which a larger number of treatment stations are present, ring lines are sometimes also used which are connected to a central supply unit. The acid liquid concentrate is manufactured or made available with the aid of special mixing apparatus in this central supply unit and is then fed into the ring line. It is led off from the ring line at the dialyzers or at the treatment stations and is then available to the dialyzer for preparing the ready-to-use dialysis solution.

A disadvantage of this procedure is that the disinfection and cleaning of such a system is laborious, expensive and pollutive and moreover that this type of concentrate supply is only economical for larger treatment centers due to the relatively high costs.

SUMMARY OF THE INVENTION

It is the underlying object of the present invention to provide a possibility of providing an acid concentrate which is associated with low costs and which can be carried out simply.

This object is satisfied by a container having the features described herein.

Provision is accordingly made that the dry concentrate located in the container is designed so that, on its solution in a liquid, preferably in water, it forms an acid liquid concentrate or a portion of an acid liquid concentration which is suitable for manufacturing a dialysis solution.

It is thus the underlying idea of the present invention to provide the acid liquid concentrate by dissolving an acid dry concentrate located in a container, e.g. in a bag or in a cartridge. The transportation of heavy canisters to the dialyzer as well as the provision of complex ring line systems can thereby be avoided. It is sufficient to fixedly connect the container in accordance with the present invention to the dialyzer or to a preferably local preparation unit, which is preferably located in spatial proximity to the dialyzer, and then to manufacture the acid liquid concentrate on site, i.e. at the treatment station, by dissolving the named dry concentrate.

The present invention thus relates to the manufacture of the acid concentrate usually used within the framework of the dialysis treatment and for manufacturing of the read-to-use dialysis solution. This acid liquid concentrate preferably comprises the ions $Na^+$, $Ca^{2+}$, $Mg^{2+}$, $K^+$, $Cl^-$ and optionally further ions and additives such as one or more acids, buffers, acetate, glucose, etc.

If a preparation unit is used, it is preferably not located at a central site, but is rather arranged locally, for example at or in the proximity of the dialyzer or treatment station. It is conceivable that one such preparation unit is provided per dialyzer.

It is thus possible in accordance with the invention, in a similar manner also to the base concentrate, to present the acid dry concentrate in a disposable container or in another receptacle preferably fixedly connectable to the dialyzer or to a preparation unit. It is conceivable that the receptacle has one or more connection elements which are connectable, preferably releasably, to one or more coupling means of the dialyzer or of the preparation unit by a plug-in connection or in another manner and independently of the type of connection. The connection between the receptacle and the dialyzer or the preparation unit is preferably made fluid-tight and releasable so that the receptacle can be removed again after its use and can be replaced with a new receptacle filled with dry concentrate.

The dry concentrate can then, for example, be brought to dissolving by apparatus already present in the dialyzer or in a preparation unit, such as pumps and air compressors, and can then be used directly for manufacturing the read-to-use dialysis solution.

Alternatively or additionally to this, local mixing units, preferably smaller mixing units, can also be used which are also called preparation units within the framework of the present invention and to which the concentrate receptacle, i.e. the container in accordance with the invention, can be connected. The dissolving of the acid concentrate takes place in this, whereby the acid liquid concentrate is produced which can then be supplied in a suitable manner to the dialyzer or can be used for manufacturing the finished dialysis solution.

The container in accordance with the invention is designed so that it has connection means by means of which the container can be coupled to a dialyzer or to a preparation unit. These connection means can be designed so that they ensure a reliable attachment of the container to the dialyzer or to the preparation unit using coupling means of the dialyzer or of the preparation unit. The coupling can be formed so that it is liquid-tight and/or gas-tight.

The connection means and the coupling means can be formed so that the container can be arranged at the dialyzer or at the preparation unit by a plug-in connection. It is also possible to make the connection means at the container and the coupling means at the dialyzer or at the preparation unit so that the coupling is achieved by a rotary movement or by a pivot movement of the container, optionally comparable with a bayonet closure.

The connection means of the container in accordance with the invention can, for example, cooperate or communicate with coupling means of the dialyzer or of another preparation unit such that, on the one hand, a connection region is established between the coupling means and the connection means by which the medium used for dissolving the dry concentrate, in particular liquid, preferably water and additionally gas, preferably air, is introduced. This introduced liquid or the introduced water as well as the introduced air or gas can then be introduced into a lower region of the container starting from the connection means of the container through a hose, through a passage, through a tube, etc. The finished liquid concentrate can preferably also be removed from the receptacle through this coupling point.

The connection means and the coupling means can furthermore form a second connection region through which a fluid, in particular a gas, and particularly preferably air, is removed from the container.

In a preferred embodiment of the invention, not only water, but also air, is introduced through the connection means of the receptacle and through the coupling means of the dialyzer or of the preparation means or through a corresponding fluid connection of these means, and further preferably through a hose or the like, into the container for the purpose of dissolving the dry concentrate.

So that this air can escape, the connection means and the coupling means have a second connection region which forms a second fluid connection between the receptacle and the dialyzer or the preparation unit and through which the air can be led off out of the container e.g. into the atmosphere or into the dialyzer or into the preparation unit and can be led off from this e.g. into the atmosphere.

An exemplary embodiment for the connection means of the container, on the one hand, and for coupling means of the dialyzer or of a preparation unit, on the other hand, can be found in EP 1 344 550 B1 to which reference is here made in full and whose disclosure content is herewith made the subject of the present invention. As can be seen from this document, the connection means of the container each have connector parts which can each be coupled to a corresponding connector part of the coupling means. These connector parts each have a passage through which, in accordance with the present invention, air and the solution medium for dissolving the dry concentrate, in particular water, flows and then moves into the container.

The other connector part of the connection means likewise has an opening or a passage which serves to lead off air out of the container during the dissolving process.

Deviating from the teaching of EP 1 344 550 B1, provision is preferably made within the framework of the present invention that a connector part serves for the supply of air and of the solvent, in particular water, as well as also for the removal of the liquid concentrate. The other connector part serves, within the framework of the present invention, only for the removal of gas or air from the container.

The named dry concentrate located in the container can, for example, comprise NaCl and/or $CaCl_2$ and/or $MgCl_2$ and/or KCl and/or further electrolyte salts and/or citric acid and/or one or more further acids and/or glucose and/or acetate or other ions or can consist of one or more of these substances.

As a further embodiment or aspect of the invention, it is possible that the container has such a volume that, in addition to the dry concentrate, liquid, preferably water, can be received or is received in a volume of 2 to 15 liters or of 4 to 15 liters, preferably in a volume of 4 to 15 liters, to manufacture the acid liquid concentrate by dissolving the dry concentrate and/or that the container has a total volume in the range from 4 to 15 liters.

It is in particular conceivable that the dry concentrate is contained in the container in a quantity such that on its dissolving in a volume of 4 to 15 liters of liquid, preferably water, a liquid concentrate results, with the dry concentrate preferably being completely dissolved. This is diluted for manufacturing the finished dialysis solution so that the substances are preferably present in the following concentration ranges with respect to the volume of the finished dialysis solution:

NaCl: 110-170 mmol/l, preferably 130-150 mmol/l
KCl: 0.7-4.3 mmol/l, preferably 1.0-4.0 mmol/l
$CaCl_2$: 0.7-2.0 mmol/l, preferably 1.0-1.75 mmol/l
$MgCl_2$: 0.3-1.2 mmol/l, preferably 0.5-1.0 mmol/l
Glucose: 0.8-2.2 g/l, preferably 1.0-2.0 g/l
Citric acid: 0.1-20 mmol/l, preferably 1.0-15.0 mmol/l, All values relate to the finished dialysis solution. It is, for example, conceivable that 34 liters of a mixture of water and the base concentrate are mixed with 1 liter of the acid liquid concentrate to obtain 35 liters of ready-to-use dialysis solution. This mixing ratio naturally applies not only to the above-named example, but can be assumed as a suitable mixing ratio in general.

The preferred volume capacity of the container in accordance with the invention is preferably in the range of 4 to 15 liters.

The dry concentrate and thus also the acid concentrate formed therefrom can comprise one, a plurality of or all of the aforesaid substances. It is also possible that the dry concentrate and thus also the acid concentrate formed therefrom comprises further than the named substances.

Provision is preferably made that the acid liquid concentrate has a pH <7.0 and/or that the dry concentrate comprises at least one acid.

It is conceivable that, in addition to the explicitly named substances, further substances are also located in the dry concentrate such as further electrolytes, buffers, acids, etc.

The container can have rigid and/or flexible walls. It is preferably made as a bag or also as a cartridge which has solid walls.

A combination of solid and flexible walls is also conceivable. The container can thus, for example, have a solid wall in the region or regions in which liquid and/or gas and/or the acid liquid concentrate is led off and a flexible wall in the remaining regions.

It is furthermore conceivable that the container is a disposable article. It is to be understood by this that the container is discarded, i.e. not reused, after the end of its useful life, i.e., for example, after approximately 1 to 3 uses or treatments. It is conceivable to deliver the containers in the form of bags or cartridges or the like, to manufacture the acid liquid concentrate therein and to use it for one or more dialysis treatments. Once it is consumed, the receptacle is thrown away.

The dry concentrate can be present in the container in an amount of 0.5 kg to 6 kg, preferably in an amount of 0.75 kg to 5.5 kg, further preferably in an amount of 1.0 kg to 5.0 kg, and particularly preferably in an amount of 1.3 to 4.2 kg. Such containers allow a problem-free handling, are easy to transport and to store and are suitable for carrying out one or more hemodialysis treatments.

It is possible that the dry concentrate is composed such that the acid liquid concentrate obtained on its solution in a volume of 2 to 15 liters, or of 4 to 15 liters, preferably in a volume of 4 to 15 liters liquid, preferably water, has a pH <7.0.

It is conceivable that no liquid substances are included in the container before the dissolving of the dry concentrate. The case is, however, also covered by the invention that at least one liquid component such as an acid is also present in the dry concentrate. The term "dry concentrate" is thus to be understood such that the dry concentrate is not in the completely dissolved state, i.e. comprises at least partly, preferably fully, one or more solids.

The container can furthermore be designed such that a volume of the acid liquid concentrate can be received or is received in the container in the range of 1 to 15 liters, preferably in the range of 2 to 14 liters, further preferably in the range of 3 to 13 liters, and particularly preferably in the range of 4 to 15 liters.

In a further embodiment of the invention, the container has at least one introduction means through which the liquid, preferably water, or the liquid, preferably water, and a gas, preferably air, can be introduced into the container for the purpose of dissolving the dry concentrate located in the container. The introduction means can, for example, be a hose, a passage, a pipe or another line.

The introduction means can generally be made such that the liquid or the liquid and the gas is/are introduced into a region of the container in which the dry concentrate is located, such as in a lower region of the container interior in the operating position.

The supply of the liquid and/or of the gas into the container must therefore be formed such that the end of the introduction means ends in the dry concentrate, which brings about the advantage that the supply of liquid or of liquid and gas may result in a swirling of the dry concentrate, whereby its dissolving is accelerated.

The supplied gas is preferably a sterile-filtered air within the framework of the present invention.

The one or more introduction means are advantageously thus dimensioned so that they project into the dry concentrate. It is thus possible that a hose or another line projects, for example, from a wall or a port region of the container into the container interior.

Provision is made in a further embodiment that the container has wall regions in at least one region between which a trough-shaped or depression-shaped region forms, with the dry concentrate being at least also present in the trough-shaped region in the operating position of the container. It can be ensured in this manner that the dry concentrate "slides on" into the named trough-shaped region and is thus present at a central position in which favorable conditions apply for the dissolving of the dry concentrate.

Provision is thus preferably made that the receptacle has at least one, or a plurality of funnel-like constrictions, and indeed in the lower end region of the receptacle. It is thus ensured that the non-dissolved dry concentrate is located directly at the point of delivery of the fluid or liquid and air during the total dissolving procedure and is to continuously swirled. The time for the complete dissolving of the concentrate is in particular reduced to a favorable time period by this measure.

The introduction means, i.e. the hose, the line or the like, preferably extends up to and into the trough-shaped region or up to and into the funnel-like constriction.

Provision can in particular be made that the introduction means extends up to and into the trough-shaped region and preferably has at least one opening, preferably at least one outlet opening and/or at least one inlet opening, in this region, with provision preferably being made that in operation a liquid, preferably water, and gas, preferably air, is introduced through the outlet opening and that in operation the acid liquid concentrate is led off out of the container through the inlet opening and/or that the outlet opening and the inlet opening are formed by one and the same opening.

Provision can furthermore be made that the introduction means has a closure element which is arranged and designed such that the penetration of the dry concentrate into the introduction means is prevented. It is ensured in this manner that no solid can enter into the introduction means, but only gas or air and/or liquid or water or the acid liquid concentrate.

The specific weight of the closure element of the introduction means preferably lies in the range <11 kN/m$^3$, preferably in the range <10 kN/m$^3$ and particularly preferably in the range of <9.7 kN/m$^3$.

In a further embodiment of the invention, the container has at least one outlet means by means of which the acid liquid concentrate can be led off from the container. This outlet means can, for example, be a hose or another line which preferably projects into the interior of the container. It is also possible to form the outlet means simply as an opening in the container.

Provision can in particular be made that the outlet means is formed as a component separate from the introduction means and/or that the introduction means and the outlet means are arranged at different positions or sides of the container, preferably at oppositely disposed sides of the container or at the same side of the container.

It is conceivable that the outlet means is partly or fully formed by the introduction means in accordance with the above-described possibilities. The introduction means and the outlet means can thus be one and the same element of the container. A hose or another line can be taken into consideration, for example. First, ultrapure water or RO water and/or preferably purified or filtered air can be conveyed through it, for example, for the purpose of dissolving the dry concentrate. If the dry concentrate is preferably completely dissolved, provision can be made that the acid liquid concentrate formed in this manner is led off through the same hose or the same line.

The acid concentrate is supplied to the dialyzer or used in the dialyzer for manufacturing a finished dialysis solution in that the acid concentrate and preferably a base concentrate is mixed with water to form the finished dialysis solution. For this purpose, one or more metering devices such as pumps or the like can be used which meter the concentrate or the concentrates in the suitable amount to the water or to the water flow which flows, for example, through a main line so that the finished dialysis solution includes the desired components in the desired concentration.

It is conceivable that first a base liquid concentrate and then the acid liquid concentrate in accordance with the invention is admixed to the RO water. Provision can be made in this respect that in each case approximately one part of the base liquid concentrate and approximately one part of the acid liquid concentrate are metered into approximately 33 parts RO water.

Provision can be made in this respect that the RO water flows through a main line which communicates with two secondary lines in one of which the base liquid concentrate is present and in the other of which the acid liquid concentrate is present or which are connected to the respective containers in which the concentrates are respectively manufactured.

Provision can furthermore be made that the container has at least one venting means which is arranged and designed such that air or another gas can escape from the container, which is preferably the case when the liquid and/or the gas is introduced into the container for the purpose of dissolving the dry concentrate.

The venting means can, for example, be formed by at least one line and/or by at least one membrane or a filter which is arranged, for example, in the container wall or in a line or the like which is connected to the container interior so that air can escape. The venting means is preferably a different component than the means for the introduction of water and air and for leading off the concentrate.

Provision can furthermore be made that the container has at least one coding by means of which the container and/or the dry concentrate and/or the liquid acid concentrate can be identified. It is thus possible, for example, that a detection unit is provided, for example, at the dialyzer or at the preparation unit or also in another device, for example, a hand-held device, by means of which the coding can be read out. A specific dissolving procedure can then be initiated to dissolve the dry concentrate in an automated or manual manner, for example, on the basis of this information. If an automated recognition of the coding takes place, provision can be made that an automatic dissolving process is initiated to dissolve the dry concentrate without any further interaction by the user. If this is concluded, provision can furthermore be made that, optionally likewise in an automated manner, a metering in of the acid concentrate takes place for manufacturing the finished dialysis solution.

It is conceivable that the dry concentrate is present in the form of a powder and/or in the form of a granulate. As already stated above, the dry concentrate can comprise only solid substances. The case is, however, also covered by the term "dry concentrate" in the sense of the present invention that liquid components are present in the container.

The connection means for coupling the container can be formed such that a connection of the container is only possible using a coupling means of a dialyzer or by means of a preparation unit or by means of a certain type of dialyzer or of a preparation unit for a dialyzer. It is thus conceivable that the connection means of the container and the coupling means of the dialyzer or of the preparation unit fit together in the sense of a key-and-lock principle or are especially adapted to one another so that a faulty coupling to dialyzers or preparation units which are not suitable or which are not provided for the use of the container is precluded.

The container can, for example, be a so-called stand-up container. Such a container is usually characterized by at least two walls which are connected to one another by a base which is preferably formed so that the container as a whole can stand. In this respect, it is conceivable that this stand-up container is used within the framework of the present invention such that the base is arranged at the top so that, for example, an upside down triangle results. This can be, but does not have to be, arranged not standing exactly vertical; a sloped arranged is also covered by the invention. Provision is, however, preferably made that the corner of the container opposite the named standing base is arranged at the bottom or in a bottom region when the container is used.

Such a stand-up container has the advantage that it is flat in the empty state since the standing base is preferably designed such that it can be folded in. In the filled state, such a stand-up container provides a comparatively large volume. The container is preferably formed in the manner of a stand-up container and includes embodiments in which the standing base has sufficient stability so that the container can theoretically stand as well as those in which this is not the case.

The stand-up container is preferably arranged so that in the inwardly folded state the standing base has an inwardly folded "base section" whose limbs are, however, of unequal length so that an asymmetrical triangle results when the container is filled or unfolded. Such an embodiment has the result that, on the filling of the container, the "standing base" located at the top is unfolded, with an only small displacement of gravity results due to the asymmetrical design of the folded standing base so that the V-shaped lower region of the container also remains in this lower position when the container is filled.

An efficient dissolving of the dry concentrate can thereby be achieved.

Provision is made in a conceivable embodiment of the invention that the container comprises two films which are sealingly connected to one another in a suitable manner. It is thus conceivable, for example, to weld the films together so that the liquid concentrate which is created by dissolving the dry concentrate can be received in the container.

It is possible to design a wall or a film as substantially straight and to design the other with a folded corner region or marginal region, which brings about the advantage that the container takes up very little space in the inwardly folded state and can receive a large volume in the unfolded state.

In a preferred embodiment of the invention, the container thus comprises exactly two films which form all the walls of the container.

The use of the container is preferably provided such that the "base" which can be formed by the fold of one of the films is arranged at the top or in an upper region on use of the container so that the oppositely disposed side of the container which is preferably triangular in a longitudinal section is arranged at the bottom.

The present invention furthermore relates to the use of a container in accordance with the present invention for manufacturing an acid liquid concentrate which in turn serves the manufacturing of a dialysis solution, preferably of a dialysis solution for hemodialysis. It is conceivable that the dialysis solution is manufactured by metering the acid liquid concentrate and optionally a base concentrate into a liquid flow or into a liquid volume, preferably comprising ultrapure water or RO water. This dialysis solution can then, optionally after the addition of further substances and optionally after a suitable temperature treatment, be used as a finished dialysis solution for carrying out a dialysis treatment, preferably a hemodialysis treatment.

The invention further relates to the use of an acid liquid concentrate located in a container in accordance with the invention for manufacturing a dialysis solution, preferably a dialysis solution, which is used for hemodialysis.

The present invention furthermore relates to a dialyzer or to a preparation unit, with the preparation unit serving the manufacture of a concentrate for a dialysis solution. Provision is made in accordance with the invention that the dialyzer or the preparation unit is coupled to a container in accordance with the invention or is suitable for coupling to such a container.

The dialyzer or the preparation unit is thus suitable to be coupled to a container in accordance with the invention via suitable coupling means. Provision is preferably made that the dialyzer or the preparation unit has means by means of which the dry concentrate located in the coupled container can be completely dissolved in order to be able to provide an acid liquid concentrate in this manner. These means can be designed such that at least one liquid, preferably ultrapure water or RO water, or at least one liquid, preferably ultrapure water or RO water, and at least one gas, preferably air, is/are introduced into the container.

The dialyzer or the preparation unit can thus have means, in particular one or more pumps or liquid sources and/or compressors or compressed air sources, or are connected or connectable to them, which are designed such that at least one liquid and/or at least one gas is/are introducible or introduced by the means into the container coupled to the dialyzer or to the preparation unit.

The solution or the acid liquid concentrate located in the container coupled to the dialyzer or to the preparation unit can furthermore be led out of the container via these means, in particular one or more pumps. The acid liquid concentrate, for example a liquid, e.g. water or a mixture of water and a base concentrate, which flows in a main line, can be metered in by means of the means in order in this way optionally to be able to manufacture a finished dialysis solution after the addition of a base concentrate.

The dialyzer or the preparation unit can have at least one metering device which is connected to the named means or includes them, with the metering device being designed such that it meters the acid liquid concentrate led off out of the container into a liquid stream or into a receptacle preferably partly or completely filled with liquid, preferably with water, for the purpose of manufacturing the dialysis solution.

Provision can furthermore be made that the dialyzer or the preparation unit has at least one main line and at least one secondary line which opens into the main line and in which or at which the at least one container in accordance with the invention is arranged. It is thus conceivable, for example, that the at least one container is arranged in a secondary line which is connected to a main line at least one point or also at two points. It is conceivable in the case of two secondary lines that water or water and air is/are supplied to the container by a secondary line leading to the receptacle and that the liquid concentrate is led off out of the receptacle through a line leading off from the receptacle.

It is equally conceivable that the secondary line is only connected to a main line at one point and the dissolving process is designed such that a liquid, preferably RO water and/or gas flows from the main line into the container and, after the dissolving of the dry concentrate, the liquid concentrate is then again conducted via the same secondary line into the main line or into another line or into a receptacle.

Furthermore, at least one control or regulation unit can be provided which is designed such that it controls or regulates the supply of liquid, preferably water, or of liquid, preferably water, and gas, preferably air, into the container and/or the removal of gas, preferably air, and/or of the acid liquid concentrate from the container in dependence on time and/or in accordance with a specific program and/or supplies or leads it off in a predefined quantity.

The dissolving process is preferably carried out so that no excess pressure or no substantial excess pressure is present in the container. Venting preferably takes place toward the atmosphere, that is the container is directly or indirectly connected to the atmosphere via the apparatus or via the preparation unit.

It is also possible that the control or regulation unit is designed such that it controls or regulates the supply of liquid and/or gas into the container and/or the removal of the solution from the container in dependence on time, i.e. for example, for a specific duration or in accordance with a specific time schedule; and/or that a specific quantity of water is added to the receptacle to obtain the desired concentrations of the substances.

It is thus conceivable, for example, that liquid, in particular water, or liquid, in particular water, and gas, in particular air, is/are supplied to the container for a predefined time or at predefined intervals and/or in a defied volume and/or mass.

The manufacture of the acid concentrate preferably does not take place continuously, but rather batch-wise. Air and water are first preferably introduced into the dry concentrate or into the container and excess air is removed again. Provision is preferably furthermore made that the liquid concentrate is led off from the container via a pump or the like after the full dissolving of the dry concentrate.

Provision is preferably made that the recipe prescribes a certain amount of water. This amount of water is then, for example, carried out in discrete portions or continuously. A water metering in the form of a plurality of 30 ml volumes which are added after one another is conceivable, for example.

Provision can furthermore be made that the control or regulation unit is designed such that the supply of liquid or of liquid and gas takes place continuously, in intervals or batch-wise. It is, for example, conceivable, to add a specific quantity of liquid water once and to introduce, continuously or once or intermittently or permanently, a gas, in particular air, into the container to accelerate the dissolving process.

The present invention moreover relates to a further embodiment of a dialyzer or of a preparation unit. Provision is made in this respect that a dialyzer or a preparation unit, with the preparation unit serving the manufacturing of a concentrate for manufacturing a dialysis solution, is designed such that the dialyzer or the preparation unit has at least one connection means by means of which a compressed air line means is connectable or connected to a liquid line means, with liquid or liquid and gas being suppliable by means of the connection means to a container including at least one dry concentrate, and with acid liquid concentrate being able to be led off out of the container by means of the connection means.

It is possible that at least one control or regulation unit is provided which is designed such that it controls or regulates the supply of liquid, preferably water, or liquid, preferably water, and gas, preferably air, into the container and/or the removal of gas, preferably of air and/or of the acid liquid concentrate out of the container and/or that the dialyzer or the preparation unit furthermore has the characterizing features in accordance with one of the claims 7 to 9. The container can in particular be a container in accordance with one of the claims 1 to 4 and/or in accordance with the above description. It is also conceivable that the dialyzer or the preparation unit is suitable for coupling to a container in accordance with one of the claims 1 to 4 and/or in accordance with the above description. The liquid can be water, in particular RO water, and the gas can in particular be air.

It is therefore in particular conceivable that a connection is provided in a dialyzer or in a preparation unit from a compressed air line to a water line which serves the supply of RO water into the container and for leading off the concentrate. In addition, this dialyzer or this preparation unit has a control and/or regulation unit having a program for the simultaneous introduction of air and water.

The present invention furthermore relates to a method for manufacturing an acid liquid concentrate which serves the manufacture of, a dialysis solution, with the method including the following steps: Coupling a container in accordance with the invention to a dialyzer or to a preparation unit; complete dissolving of the dry concentrate; and removal of the acid liquid concentrate obtained by the complete dissolving of the dry concentrate from the container.

It is conceivable that a liquid, preferably water, or a liquid, preferably water, and gas, preferably air, are introduced into the container for the purpose of dissolving the dry concentrate.

Provision can furthermore be made that first a liquid, preferably water, and subsequently gas, preferably air, or liquid, preferably water, and gas, preferably air, are simultaneously introduced into the container for the purpose of dissolving the dry concentrate.

It is possible that the liquid, preferably water, or the liquid, preferably water, and the gas, preferably air, is/are conveyed for a specific time period and/or in a specific volume or mass and/or by a specific number of conveying movements and/or by a specific operating period of a conveying unit. The liquid or the liquid and the gas can therefore be conveyed for a specific time period by a specific number of conveying movements of a conveying unit such as a pump into a container. It is conceivable that, for example, a specific number of balance chamber fillings of the dialyzer is used to fill the container in accordance with the invention with a liquid or water.

On the use of a balance chamber of a dialyzer as a metering system for adding the solvent and/or for removing the liquid concentrate, it is not possible to add any desired volumes, but rather only whole-number multiples of the balance chamber volume. To achieve the correct concentration of the finished dialysis solution with a predefined amount of salt, the concentrations obtained on the dissolving are taken into account in the dilution of the concentrate. A similar process is known form EP 0 548 537 A2 to which reference is made in this respect.

If, for example, the desired volume of the balance chamber or metering chamber amounts to 30 ml, the exact volume of the chamber may differ due to a tolerance in the range from −1 ml to +2 ml. This exact volume of the balance chamber can amount to 29.50 ml as an example. This value is present in the dialyzer.

If the recipe now prescribed a water quantity of, for example, 4500 ml, there results from 4500 ml: 29.5 ml=152.542 switchovers of the metering system. This corresponds to 152 switchovers and a residue of 29.5 ml*0.52=15.99 ml. These 15.99 ml are taken into account in the calculation of the actual mixing ratio.

The pumping volume of the concentrate pump is then calculated from the mixing ratio in the bag or in the receptacle calculated in this manner and is communicated to said pump.

The aforesaid values are naturally only of an exemplary nature and should only illustrate the general procedure as can be used on the use of the balance chamber system as a metering means. This procedure is likewise part of the present invention.

Provision can furthermore be made that the transmission or the absorption of the solution located in the container is measured and the extent to which the dry concentrate is dissolved is determined in dependence thereon. If, for example, the transmission reaches a specific value, it can be concluded from this that the dry concentrate is completely dissolved. The acid liquid concentrate formed in this manner can then be led off from the container and used for manufacturing a dialysis solution.

It is conceivable that the liquid or the liquid and the gas is/are introduced continuously, at intervals or batch-wise into the container and/or the solution is led off from the container continuously, at intervals or batch-wise. Provision is made that a leading off of the solution from the receptacle only takes place when the dry concentrate is completely dissolved.

It is possible that the supply of liquid, preferably of water, or of liquid, preferably water, and gas, preferably air, into the container takes place such that the dry concentrate is completely immersed in liquid, preferably water, and/or such that the dry concentrate is moved, preferably swirled, through the gas, preferably air.

The quantity of the water supplied results, for example, from the composition of the powder/granulate. A specific quantity of powder or granulate has to be mixed with a specific quantity of water. The powder/granulate must be able to be completely dissolved by this quantity of water. On the dissolving or on the filling with water and on the introduction of the air, the receptacle is preferably open toward the atmosphere, and indeed preferably via the corresponding coupler of the dialyzer or of the preparation unit.

It is preferred if the solution located in the container, i.e. the acid liquid concentrate, is only led off from the container when the dry concentrate located in the container is completely dissolved. A complete dissolving of the dry concentrate is to be aimed for, not only in order ideally to utilize the material of the dry concentrate, but also to provide a reproducible composition of the acid concentrate.

BRIEF DESCRIPTION OF THE DRAWINGS

Further details and advantages of the invention result from an embodiment shown in the drawing. There are shown.

DETAILED DESCRIPTION OF THE PREFERRED EMBODIMENTS

Figure 1:
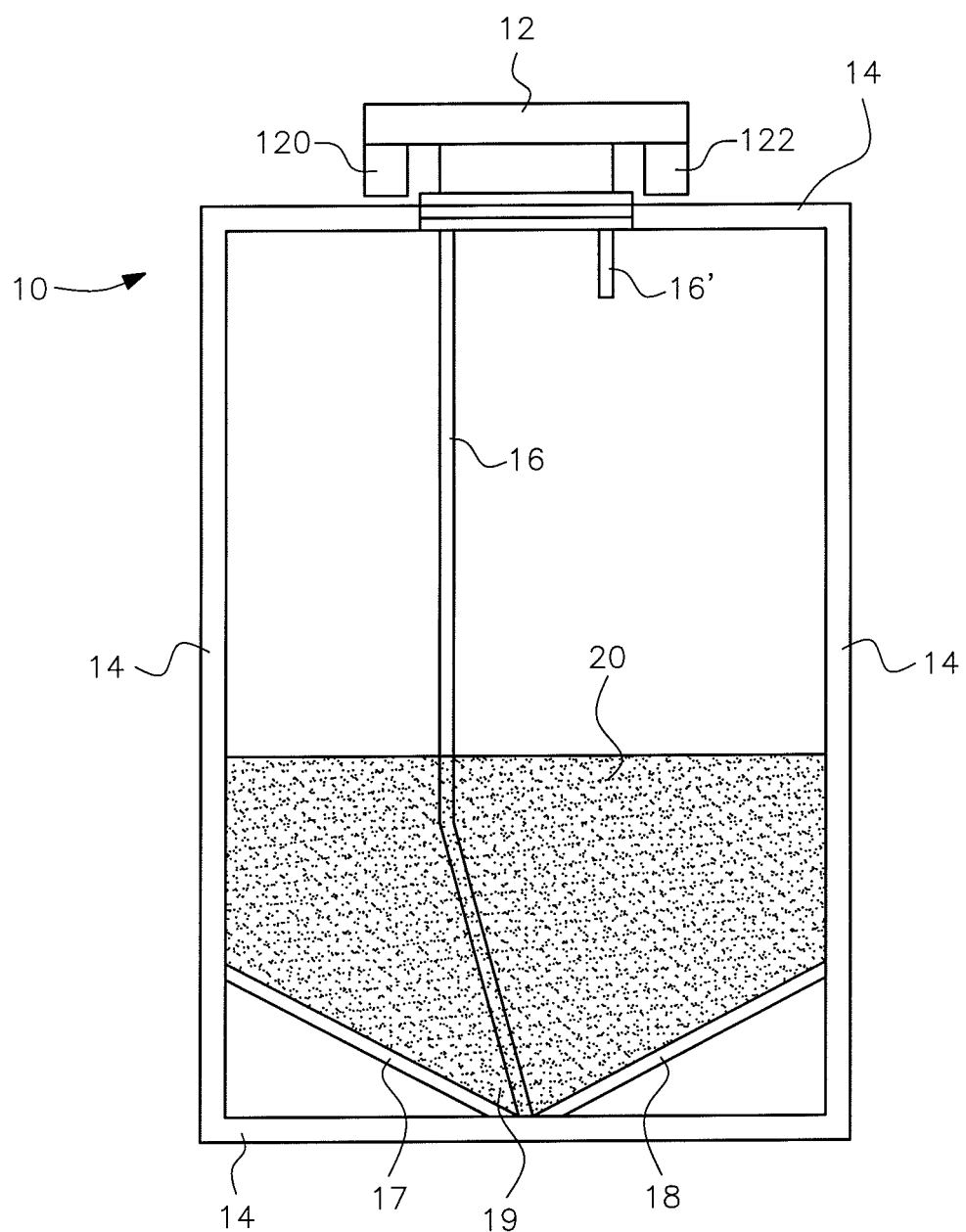
FIG. 1: a schematic view of a container in accordance with the invention which is partly filled with dry concentrate.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The container 10 is designed as a bag 10 which has flexible walls 14. The bag 10 or its walls can comprise a plastic which is preferably made transparent.

The following statements are not restricted to a bag, but can rather equally apply to any other receptacle such as a cartridge with rigid walls.

In the region of the bag 10 at the bottom in the operating position, two wall sections 17, 18 are located which are both designed as sloping with respect to the horizontal and are made falling respectively from the outside to the inside and form a trough-shaped region 19 between them which forms the bottommost point or region in which the dry concentrate 20 is located in the inner container space.

As can further be seen from the Figure, the container 10 is not completely filled with dry concentrate 20, but rather only in part.

In the embodiment shown, less than half the container 10 is filled with dry concentrate 20. Air or another gas is located above this bulk material.

The dry concentrate comprises the following substances: electrolytes, glucose and citric acid or another suitable acid in solid or liquid form.

The name electrolytes can be selected from the group NaCl, KCl, $CaCl_2$, $MgCl_2$. Conceivable amounts relating to a liter of the finished dialysis solution can be in the range from 130-150 mmol NaCl, 1-4 mmol KCl, 1-1.75 mmol $CaCl_2$ and 0.5-1 mmol $MgCl_2$. This value can be in the range from 1 mmol/l-15 mmol/l for citric acid.

Glucose can be present in the dry concentrate in a quantity such that a glucose concentration in the range of 1-2 mmol/l results in the ready-to-use dialysis solution.

A possible procedure comprises weighing out the named components individually and forming a granulate from all components which is then poured into the container or bag 10 as a dry concentrate 20.

The bag 10 can have a volume or an intake capacity of approximately 4-15 liters of the acid liquid concentrate which is formed by the solution of the dry concentrate. This quantity can be sufficient for 1-3 hemodialysis treatments.

The bag 10 has a special connection element 12 in its region shown at the top in the Figure with which the bag can be suspended at a dialyzer or at a filling station which is also called a preparation unit within the framework of the present invention. The connection element 12 can be made such that it can be connected, preferably in a fluid-tight and/or gas-tight manner, to a special coupler of the dialyzer or of a preparation unit. This connection can be established, for example, by a simple plugging on or by a rotary movement or by a screw connection.

After establishing this connection, liquid and/or gas can be introduced into the bag 10 by means of the line 16. If the dry concentrate is completely dissolved, the acid liquid concentrate can likewise be drawn out of the bag 10 by means of the line 16. The line 16 projects, starting from an upper container wall, from above into the interior of the container and down to and into the lowest point of the inner space of the receptacle 10 or into the dry concentrate present there.

The dry concentrate containing salt can be present in the bag 10 in a quantity of, for example, 1.3-4.2 kg.

As can further be seen from FIG. 1 and was already mentioned above, the bag has an inflow 16 which is formed in the manner of a hose 16 and whose open end lies at the above-named lowest point 19 of the bag 10.

The inflow or the hose 16 is provided in its end region projecting into the container with a cap, a plug, a membrane or the like as protection to prevent the penetration of the dry concentrate into the interior of the hose 16. The specific weight of this closure is preferably in the range <9.7 $kN/m^3$.

The filling with water, the introduction of air and the drawing off of the liquid concentrate takes place through the line 16.

The reference numeral 16' shows an element which serves as a venting to the atmosphere during the filling of the container. After the filling or after the dissolving of the dry concentrate, this venting 16' can be closed. This means that the element 16' has no function during the treatment.

Even though the element 16' is shown as a short line element in FIG. 1, provision is preferably made that no line 16' is present, but rather only an element such as a filter, etc. via which air can escape from the interior of the container 10. The container 10 thus preferably has only exactly one line 16 which serves the supply of water and gas and the leading off of the liquid concentrate.

On the emptying of the container in the final stage of the treatment, suction takes place at both outlets 16 and 16' to empty the container as quickly as possible.

Instead of the element 16' or in addition thereto, a filter can be seated in the connection means 12 which prevents powder from moving out of the bag during transportation.

The produced liquid concentrate can be mixed with a volume of water, preferably RO water, to be able to produce the finished dialysis solution. The base liquid concentrate, which can likewise be obtained by dissolving a dry concentrate in a container coupled to the dialyzer or to a preparation unit, can be metered in before or after the addition of the acid liquid concentrate.

It is generally covered by the invention that the container containing the base concentrate is arranged spatially separate from the container which contains the acid dry concentrate. The case is, however, also covered by the invention that both containers are connected to one another and optionally form different compartments or chambers of a common container or bag.

To allow the escape of air from the container on its filling with water and/or air, a venting element is provided—as stated—which can be connected to the dialyzer or to the preparation unit. This can be formed by a filter, with this preferably being arranged in the bag wall or in the region of the connection means 12. This filter should be made such that it allows air and liquid to pass through, but no powder or granulate so that it cannot unintentionally move out of the receptacle.

To be able to carry out a clear identification of the bag, it is conceivable that it is formed with a coding such as a barcode, a 2-matrix code or RFID. It is conceivable that the dialyzer and/or a preparation unit has a reading unit for manufacturing the acid liquid concentrate by means of which this coding can be detected or read out. Based on this information, a method for dissolving the dry concentrate 20 in the bag 10 can be initiated, preferably automatically, by the dialyzer or by the preparation unit.

It is conceivable in this respect that the details of the method depend on the named bag coding or container coding. This can apply, for example, to the quantity of the added water or of the added water and the air for dissolving the dry concentrate, to the duration of the dissolving procedure, to the question whether the dissolving procedure is assisted by the supply of air, to the order of the addition of air and water, to the question whether a continuous, an intermittent or a single (batch-wise) dissolving procedure takes place, etc.

Conductivity limit values can furthermore be set on the basis of the coding.

A possible procedure of the dissolving process can be designed, for example, such that first water, preferably RO water, is added into the bag 10 through the hose 16 at a water temperature of 37° C. to 85° C.

The water flow can be in a range up to 1200 ml/mm.

In a second subsequent phase, air can preferably then likewise be introduced via the line 16 into the bag 10 for a specific period.

Alternatively to this, the introduction of water and air into the container can take place simultaneously.

It is also possible to introduce air into the container simultaneously with the water, then to stop the water inflow and to continue the water supply, preferably up to the complete dissolving of the salt or of the dry concentrate 20.

So much water or any other liquid can generally be added into the bag 10 or container 10 that it is completely filled or is only partly filled.

The filling of the bag 10 with water can take place, for example, by a whole-number number of balance chamber fillings of the balance chamber/metering chamber of a dialyzer. The actual filling volume of the bag 10 can then be determined with the aid of the known balance chamber volume. The concentrations of the individual substances result from the ratio of powder or granulate to water. Any other metering possibility such as a pump, etc. can be used for filling the bag with water.

The duration of the supply of the gas, which is preferably purified air or filtered air, can be in dependence on the filling volume and/or depend on the airflow.

In an embodiment of the invention, a timer is provided which carries out the filling or preparation of the acid liquid concentrate after the end of the last dialysis treatment (AutoOFF) or before the start of the dialysis (AutoON). The use of a timer for the preparation unit, which is also called a filling station, is possible.

If a plurality of dialysis treatments are carried out after one another with the same bag 10, it is possible to carry out an intermediate disinfection between the treatments. It is conceivable to do the filling before the purging, with no contamination risk being present since it is the primary circuit.

A "range determination" is furthermore possible, i.e. a determination of the possible time of use for the optimum utilization of the acid liquid concentrate, and is also covered by the invention.

Instead of a canister with liquid acid concentrate, in particular for bicarbonate dialysis, a bag or another container is used with a dry salt concentrate in accordance with the invention. This bag or container is filled at the dialyzer or at a filling station, preferably with a defined quantity of water for the dialysis, and is preferably dissolved by the introduction of air filtered to be sterile. After the dissolving process, an acid concentrate is available which corresponds to the demands in accordance with EN 13867:2002 in a preferred embodiment of the invention.

Figure 2:
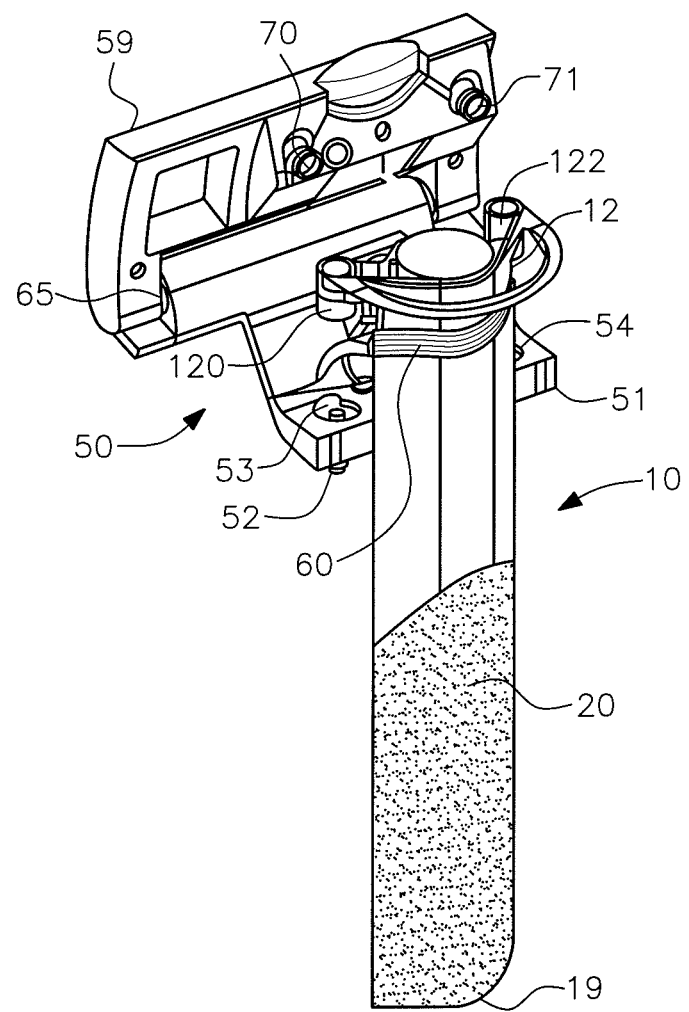
FIG. 2: a perspective view of a receptacle in accordance with the invention as well as a coupling region of a dialyzer or of a preparation unit before the coupling of the receptacle.

FIG. 2 shows an exemplary embodiment of the container in accordance with the invention with the connection means 12 which serves the coupling to the coupling means of a preparation unit or of a dialyzer.

The arrangement which can be seen from FIG. 2 represents in a preferred embodiment an arrangement in accordance with the invention for the coupling of a container 10 to the dialyzer or to a preparation unit which is generally marked by the reference numeral 50.

Air and water can be introduced through the port 52 of the unit or of the preparation unit by the connection means 12 to the container 10 and through the hose 16 into the lower region of the container. For this purpose, a connection of the port 52 to the connection 120 at the container side takes place.

The container 10 or its connection means 12 is connected via a further coupler or connector 122 to the dialysis machine or to the preparation machine. The correspondingly associated line is marked by the reference numeral 51.

It is connected to the element 16' of the receptacle.

Air is drawn out of the container through the port or the line 51 during the dissolving process or during the filling process of the container with water and air.

Different from the teaching known from EP 1 344 550 B1, the line 52 or the line 16 in accordance with the present invention does not only serve the supply of water and air, but also the leading off of the dissolved concentrate. It is drawn off through the line 16 and the line 52 by means of a suitable conveying means, for example by means of a pump, and is then diluted at a suitable point in the dialyzer or in the preparation unit so that, optionally after adding a base concentrate, a finished dialysis solution can be provided. This means that the flow path through the connection means and the coupling means as well as through hose of the water used for the dissolving at least regionally corresponds to that via which the liquid concentrate is led off. One and the same pump can also be used to supply the water, on the one hand, and to lead off the liquid concentrate, on the other hand.

As can be seen from FIG. 2, the ports or the lines 51, 52 have stubs onto which the connectors 120, 122 of the receptacle 10 are placed, and preferably plugged, so that receiving regions of the connectors 120, 122 receive the stubs. For this purpose, recesses or receivers 53, 54 are arranged at the unit or at the preparation unit into which the named stubs project and into which the corresponding connectors 120, 122 are inserted when the container 10 is coupled. In the coupled state, the stubs project into receivers of the connectors 120, 122 or are least connected therewith such that a fluid-tight connection is established.

The connector 120 is in fluid communication with the hose 16 and the connector 122 is in fluid communication with the element 16' or with a filter of the receptacle. Such a connection can, for example, be achieved by a groove or the like in the wall of the connectors 120, 122, as is described in EP 1 344 550 B1. A chamber which is likewise described in more detail in DEP 1 344 550 B1 can be located between the connector 120, 122 and the line 16 and the element 16'.

As stated, the element 16' is preferably not a hose or the like, but rather only a means which allows the air and optionally liquid to pass and holds back the dry powder/ granulate.

Accordingly, water and air can be supplied to the container 10 and the liquid concentrate can be led off out of the container 10 via the line 52 at the unit side and via the connector 120. Air can be removed or can escape from the container via the line 51 at the unit side and the connector 122.

In the installed state of the receptacle 10, the cover 59 of the unit or of the preparation unit pivotable about the axis 65 is then folded down, i.e. after the coupling of the receptacle 10, so that the stubs 70, 71 arranged at the cover 59 press from above onto the connectors 120, 122 of the connection means 12 and hold them in the coupled position. If no receptacle is used, the stubs 70, 71 can engage into the cut-outs 53, 54 so that a fluid-tight connection likewise results. A purging process can be carried out in this position of the cover.

The reference numeral 60 finally marks the end region of the bag 10 which is sealingly connected to the connection element 12.

Figure 3:
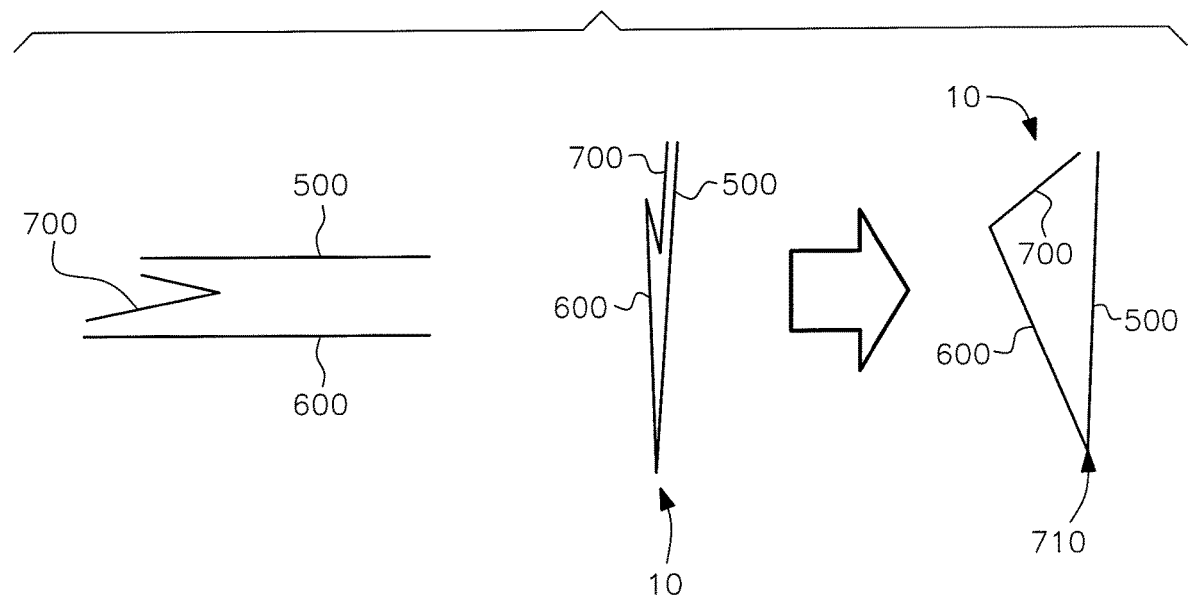
FIG. 3: a schematic view of an embodiment of the container in accordance with the invention during manufacture and well as during the opening procedure.

FIG. 3 shows a first film with the reference film 500 and a second film of an embodiment of the container 10 with the reference numeral 600. A folded region which connects the two films 500 and 600 is marked by the reference numerals 700. This folded region 700 can be designed as a separate part or can be connected in one piece to one of the films 500, 600. As can be seen from FIG. 3, the folded region 700 is formed by two limbs which are arranged acutely to one another, but do not have the same length.

FIG. 3 furthermore shows the opening process of the container from the folded state shown to the left of the arrow and in the unfolded state shown to the right of the arrow.

It is achieved by the limbs of the fold region 700 of unequal lengths that on the unfolding the center of gravity moves less than with limbs of equal length so that the V-shaped tip of the container shown by the reference numeral 710 remains at the bottom, which is of importance for the dissolving process.

The term "film" used within the framework of the present invention is to be interpreted generally and includes any wall material of the container. It can be made as elastic, flexible, etc.

The films 500, 600 and the fold 700 or the corner region 700 can comprise the same material.

Figure 4:
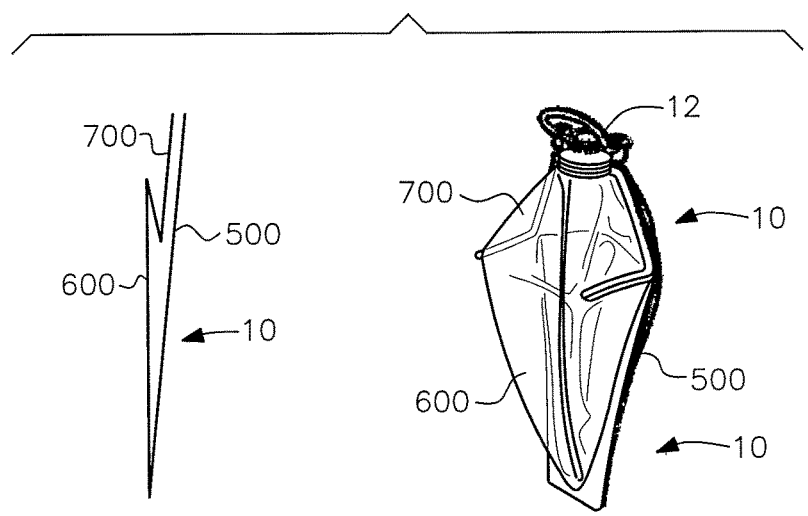
FIG. 4: a longitudinal sectional view through a container in accordance with the invention as well as a perspective view of the container in accordance with the invention.

FIG. 4, left hand illustration, shows the container in accordance with FIG. 3 in a longitudinal sectional representation and in a perspective view. The connection means 12 by means of which the container can be coupled to a dialyzer or to a preparation unit for the acid concentrate is arranged in the upper region of the container. This connection means is in fluid-tight connection with the adjacent films or wall regions of the container 10.

As can be seen from FIG. 4, a wall of the container is formed by a film and the other wall of the container by the other film which has the fold-like section. It can be seen from the Figures that the container takes up relatively little space in the folded state, but has a large intake volume for the dry concentrate or for the dissolved concentrate in the unfolded state.

Provision is made in a preferred embodiment of the invention that the container or its walls is/are manufactured exactly from two films.

Figure 5:
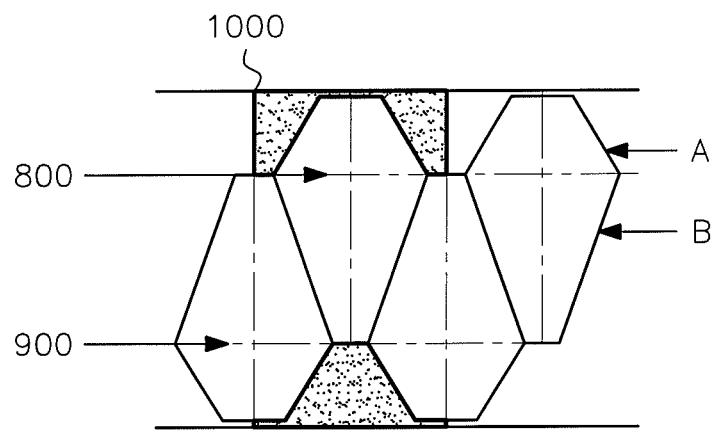
FIG. 5: a plan view of the film web for manufacturing the container.

FIG. 5 shows the film web which comprises two rows 800, 900 in a plan view. As can be seen from the Figure, the film sections for forming the container walls are formed in trapezoidal shape in a plan view and are arranged in the two webs such that the lower row 900 of the trapezoidal sections is upside down with respect to the upper row 800 of the trapezoidal sections, i.e. is standing on its head. This allows a good utilization of the film material.

As can further be seen from FIG. 5, the clippings 1000 are kept relatively small in this manner and are preferably likewise not located between the mutually adjacent trapezoids.

As is marked by the reference symbol A, the welding is produced in one step in accordance with the shown pattern M and the cutting of the films takes place in a step B following it likewise in accordance with the pattern M.

Figure 6:
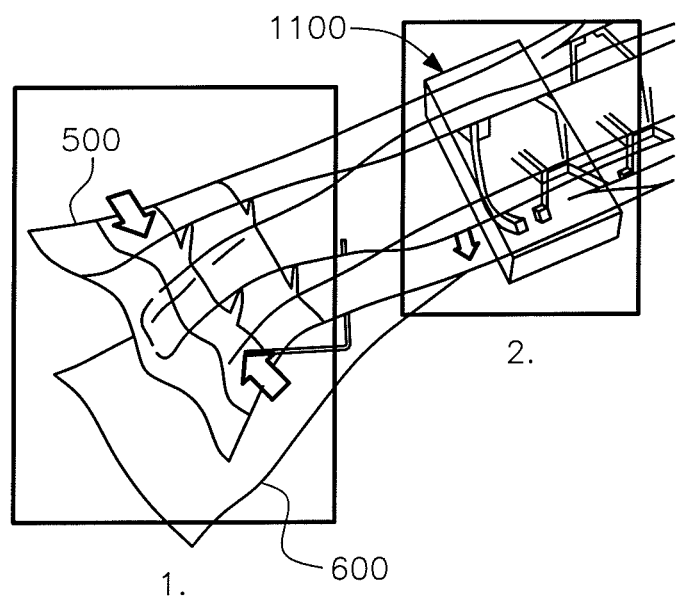
FIGS. 6, 7: schematic representations of the manufacturing process.

FIG. 6 shows the films 500, 600 which form the container in a perspective representation. As can be seen from FIG. 5 and as indicated by arrows, the upper one of the films 500 is first folded in step 1 and then welded to the lower film web 600 in step 2. The step of the cutting of the two films to produce mutually separate containers is not shown in FIG. 5. The reference numeral 1100 marks the apparatus for welding the respective film sections.

In a preferred embodiment of the invention, the individual films are each multilayer films, preferably two-layer films. One layer represents a sealing layer which has a low melting temperature. The other layer has a higher melting temperature in respect to this and has a mechanical strength or resistance which is good relative thereto.

The use of polyamide (high melting temperature, good resistance properties, transparent and visually appealing) and polyethylene (lower melting temperature, easy to weld) is conceivable. Such a two-layer film represents a good option for manufacturing the container in accordance with the invention.

The thickness of the films is preferably 200 micrometers and the dimensioning of the films is carried out in that the filled container can take up a volume of 5 liters.

Figure 7:
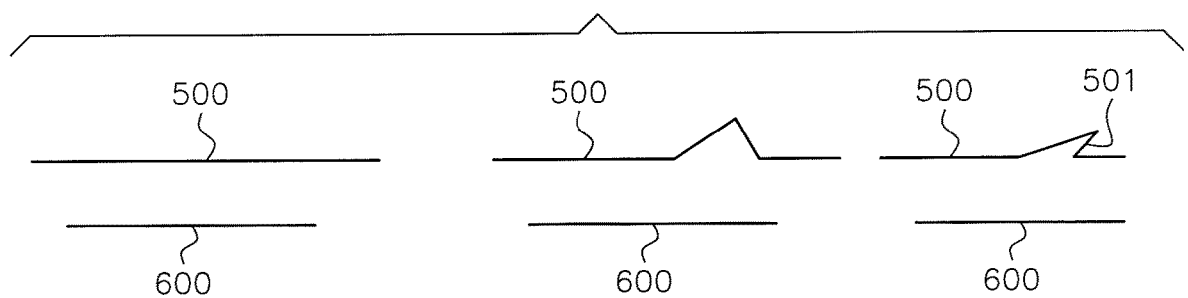

FIG. 7 shows the two films 500, 600 which form the later walls of the container in the left hand illustration. In a first method step, the films are rolled off (FIG. 7, left hand illustration). A fold or a kink is then produced in one of the films 500, as can be seen from FIG. 7, middle and right hand representation. This kink is carried out such that the length of the two films in the kinked state of the film 500 is substantially identical. The region formed by two limbs 501 forms a wall of the container 10; the further walls are formed by the adjacent sections of the film 500 and by the film 600.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A container comprising:
   at least one dry concentrate, the dry concentrate being provided so that the dry concentrate forms at least one acid liquid concentrate or a part of an acid liquid concentrate which is suitable for manufacturing at least one dialysis solution on a dissolving thereof in a liquid;
   at least one connector with which the container is coupleable to a dialyzer or to a preparation unit for the acid liquid concentrate;
   a first film and a second film which form walls of the container, with one of the first film and the second film having a folded section in an empty state of the container which forms one of the walls of the container in a filled state of the container, with the folded section being formed by two limbs which are arranged acutely to one another, and which have a different length from one another, and with the folded section connecting the first film and the second film which form the walls of the container; and
   wall regions which face toward one another in at least one region and between which a trough-shaped region or a recess is formed, with the dry concentrate being at least also present in the trough-shaped region or in the recess in an operating position of the container,
   with the two opposite walls of the container being the first film and the second film, and the base being the folded section, so that an asymmetrical triangle results when the container is filled or unfolded.

2. The container in accordance with claim 1, wherein the folded section is configured as a separate part or is connected in one piece to one of the first film and the second film.

3. The container in accordance with claim 1, wherein the container is configured as a stand-up container.

4. The container in accordance with claim 3, wherein the stand-up container has a stand-up section arranged at a top thereof during use of the container.

5. The container in accordance with claim 1, wherein the first film and the second film and the folded section, or a corner region thereof, have a same material of construction.

6. The container in accordance with claim 1, wherein a thickness of the first film and the second film is 200 micrometres and a dimensioning of the first film and the second film is such that the filled container occupies a volume of 5 liters.

7. The container according to claim 1, wherein the acid liquid concentrate is associated with a dialysis solution for hemodialysis.

8. The container according to claim 1, wherein the liquid is water.

* * * * *